United States Patent

Plant Pat. 3,836

Patented Mar. 9, 1976

3,836

ORCHID PLANT (FUGUE)

Maurice Lecoufle and Michel Vacherot, Boissy-St.-Leger, France, assignors to Les Petits-Fils et Fils de Vacherot & Lecoufle, Boissy-St.-Leger, France Filed Nov. 20, 1974, Ser. No. 525,405

Claims priority, application France, Nov. 29, 1973, 7342577

Int. Cl. A01h *5/00*

U.S. Cl. Plt.—68 1 Claim

ABSTRACT OF THE DISCLOSURE

A new variety of orchid of the species Cymbidium characterized by its vigorous and floriferous growth habit, its medium size permitting a good planting density, and its abundant production of erect stems bearing regularly spaced flowers of good size having long peduncles, excellent texture and durability and very attractive coloring, the petals and sepals being of Rose pink lightly veined with Rhodamine purple and the labellum being of the same Rose pink with whitish margins and having a light yellow color on the beard or callosities at its upper center, the pink areas being freckled with peony purple points. The natural period of flowering of this new variety is from mid-Novemver until the end of December with full production occurring about the 10th to 15th of December.

BACKGROUND OF THE INVENTION

Our new variety of orchid plant is a selection from seedlings produced by our cross-breeding of the Cymbidiums Kurun and Yule Log (both unpatented) at Boissy-Saint-Leger, France, with the object of producing a particularly early hybrid which would flower regularly from mid-November until the end of December, in order to supply the heavy end-of-year demand, and also to improve the outstanding qualities of the Cymbidium Kurun. This new variety was selected for propagation because of its exceptional qualities largely fulfilling our principal objectives and asexual reproduction of this new plant has been carried on by us at Boissy-Saint-Leger, France, by meristematic tissue culture, to ensure that all of its distinctive and advantageous characteristics are fixed, and successive generations of mericlones of this new variety of orchid have demonstrated that its distinguishing characteristics are firmly fixed and hold true from generation to generation.

As the generic identification of this new orchid variety, we have adopted the name Fugue. As a commercial name, this cultivar will be know as Valecir.

DESCRIPTION OF THE DRAWINGS

Our new variety or orchid plant is illustrated by the accompanying drawings, in which.

DESCRIPTION OF THE NEW VARIETY OF ORCHID

Figure 1:
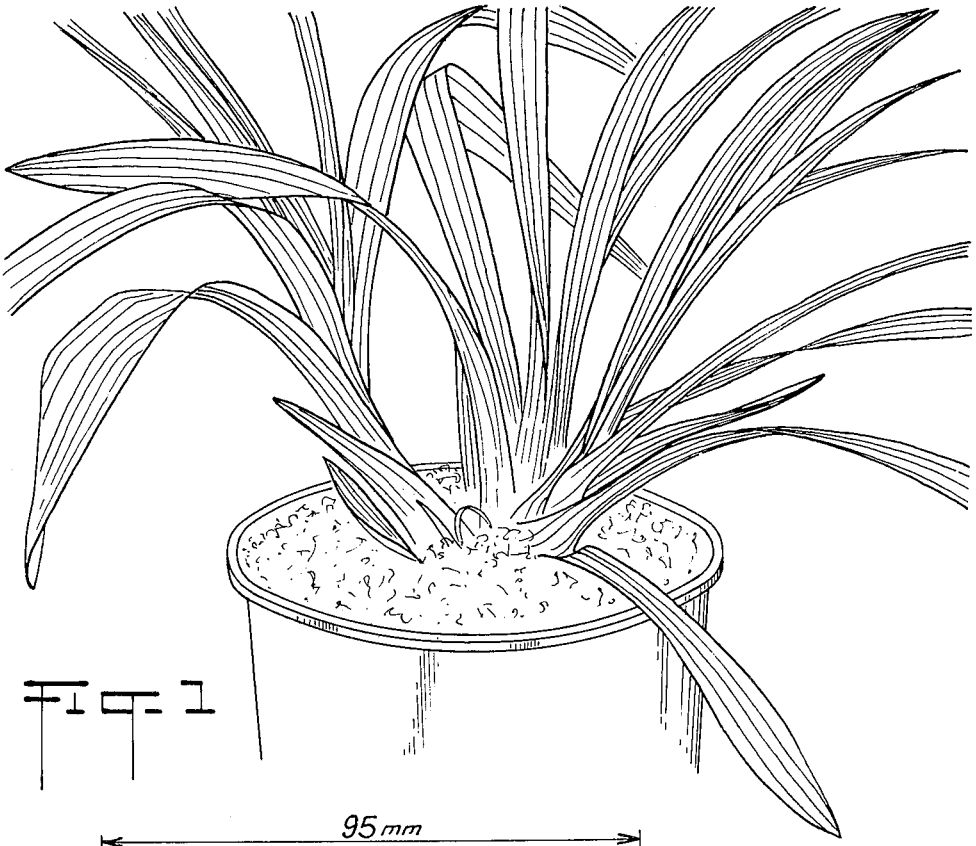
FIG. 1 is a sketch which shows a typical adult plant of the cultivar.
Figure 3:
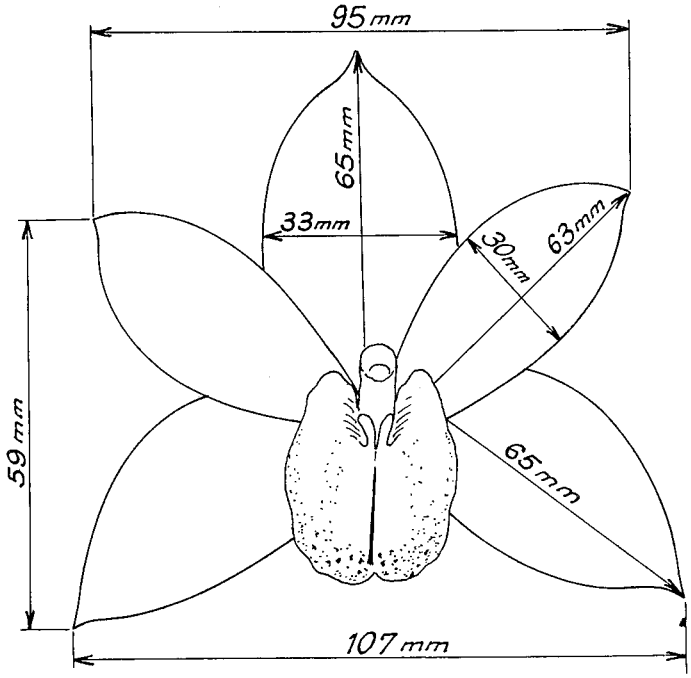
FIG. 3 is a sketch of a flower of this cultivar illustrating its form and principal dimensions.
Figure 2:
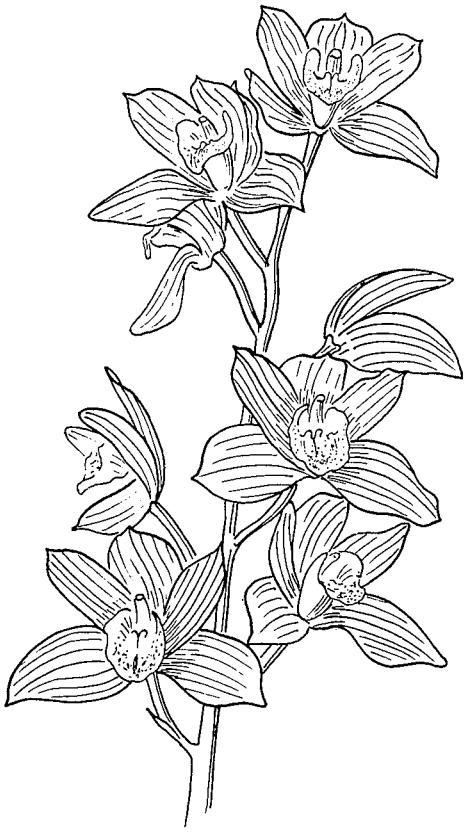
FIG. 2 is a sketch of a typical stalk or stem with open flowers.
Figure 4:
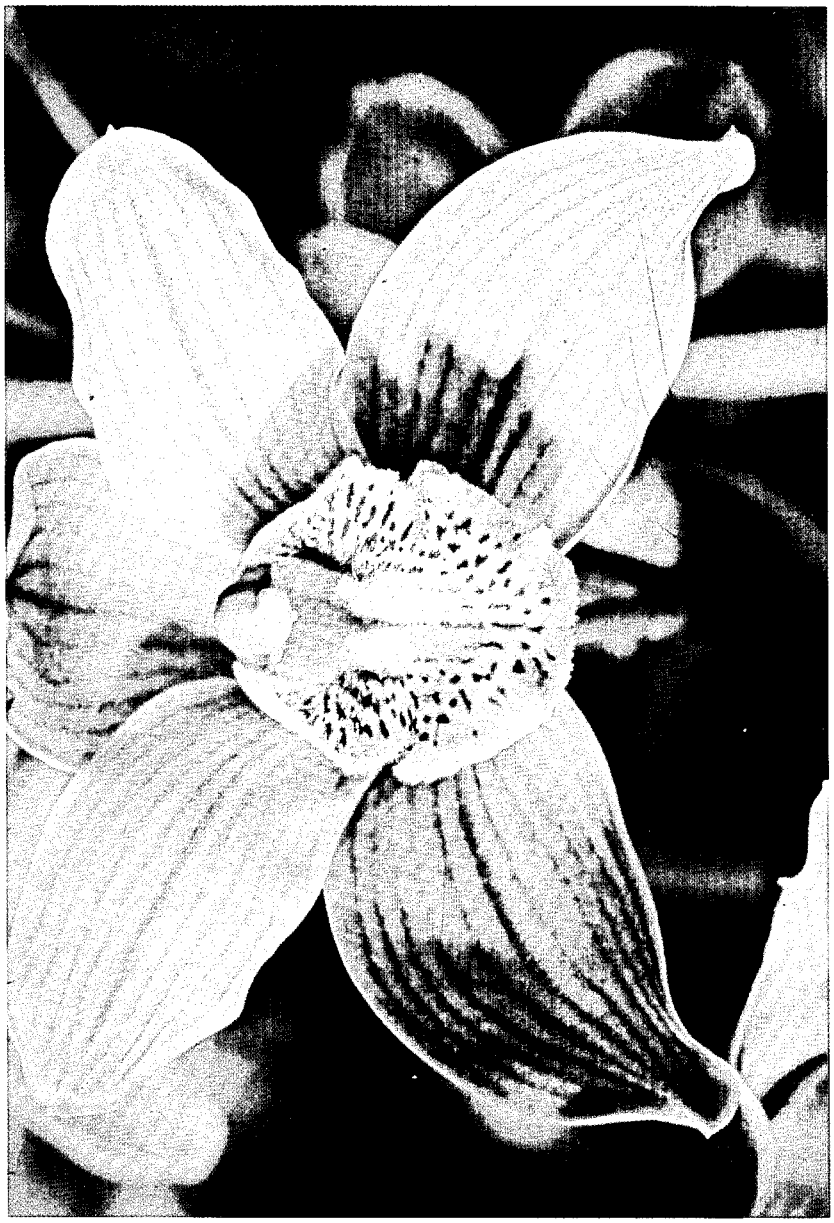
FIG. 4 is a full color photographic view of a typical flower of the new plant with the color reproduction being as accurate as can be reasonably obtained by conventional photographic procedures.

The following is a detailed description of our new variety of orchid plant with color designations according to the R.H.S. Colour Chart (RHS) and Horticultural Colour Chart (HCC) published by The Royal Horticultural Society of London, England.

*The plant*

When young, this plant is not particularly distinguishable from several other Cymbidium plants. When it is adult, however, its special characteristics become apparent to distinguish this plant from all others.

Origin: Seedling.

Parentage:

Seed Parent—Cymbidium Kurun (unpatented).

Pollen Parent—Cymbidium Yule Log (unpatented).

Classification:

Botanic—Cymbidium hybrid.

Commercial—Cymbidium mericlone.

Form: Herbaceous plants.

Height: About 120 cm., sometimes more.

Bulb:

Size: As the front bulb of the adult plant, about 7 cm. wide.

Number: A plant is adult when it has at least three well formed bulbs with leaves. Bulbs increase in number each year thereafter.

Stems: The primary bulb of an adult plant carries one or two flowering stems, eventually supporting only one stem or sometimes more than two.

Foliage:

Number of leaves: Five pairs of alternately opposed leaves on each bulb.

Size of leaves: Length—From 35 to 120 cm., sometimes longer. Width—4 cm. at largest part.

Petioles: The base of each leaf, where attached to the bulb, is about 15 cm. long. A callus in the form of a dark line or bar forms the junction between the leaf itself and its petiole.

Venation: From base to tip.

Color: The leaf is of a dark green color and has a well accentuated central rib. The petiole, of slightly lighter green color, has inwardly curved edges.

Stem: 100 to 120 cm. in length, the first flower appearing at about 60 to 70 cm. from the base of the stem. The stem is entirely surrounded with amplexicaul bracts up to about 10 to 20 cm. from the first flower.

*The flower*

Blooming habit: Recurrent. The plant flowers regularly from mid-November until the end of December with full production of blossoms occurring about the 10th to 15th of December.

Borne: In a racemose manner on a main stem 100 to 120 cm. in length, each flower being carried by a peduncle forming an acute angle with the stem. The first flower appears at about 60 to 70 cm. from the base of the stem and the distance between flowers, which can be alternate, can range between 0 and 75 cm., but it is usually from 2 to 6 cm. The number of flowers on a stem is about 15 for an adult plant and, at each flower peduncle, there is an amplexical bract embroyo which for the first flower is quite long and for the last flower extremely short.

Average size: Large. 107 mm. from tip to tip of the lateral sepals; 95 mm. from tip to tip of the petals; and 59 mm. between the tips of adjacent petals and sepals.

Sepals: Length—65 mm. Width—Lateral sepals: 35 mm.; dorsal sepal: 33 mm.

Petals: Length—63 mm. Width— 30 mm.

Labellum: 30 mm. wide and 42 mm. long.

Gynostemium: About 45 to 55 mm. long.

Shape of petals and sepals: Generally elliptic with cuspidate tips.

Shape of labellum: Generally oval, bifid adjacent the gynostemium with rearwardly extending lobes, one on each side of the column.

Color:

Petals and sepals: Rose Pink 427 (HCC), with the ends of the sepals being slightly darker, and with base to tip venation of Rhodamine Purple 29/2 (HCC), 72D (RHS).

Labellum: Rose Pink 427 (HCC), with whitish margins and light yellow on the callosities at upper center, the tongue having a light vertical Peony purple 729 (HCC) stripe or line of about 2 cm. long on the central line of symmetry and a sprinkling of small Peony Purple dots overall but the lateral margins of the lip.

Gynostemium: The upper side, on its uppermost central part, is entirely of the same Rhodamine pink coloring of the labellum, while the two lateral parts are almost colorless where they are covered by the lateral wings of the labellum. The underneath of the gynecium is marked with small dots of the same color as the dots on the labellum.

Peduncle: Length—In general, about 55 to 65 mm. The last flower has a very long peduncle, extending upwardly about 10 to 14 cm. to terminate the stem.

A cytological study of this plant has shown it to be triploid, a condition or characteristic which partcularly distinguishes this new orchid variety from all others.

Outstanding and distinctive characteristics of our new variety of orchid plant reside in its vigorous growth and rapid production of new bulbs which produces plants of medium size, and good plant density with many erect flowering stems of excellent appearance, the regular spacing of the flowers with long peduncles which permit them to be well separated, the early production of flowers of good size with excellent texture and durability, the attractive and very commercial pink and purple coloration of the flowers, and the mid-November to late December natural flowering period which gives this variety a distinguishing commercial advantage.

It wll be understood that the measurements and colors of this new plant can vary to an important extent considering the conditions of growth and the quantity of light given to the flower.

We claim:

1. A new and distinctive variety of orchid plant of the species Cymbidium substantially as herein shown and described, characterized particularly by its vigorous, rapidly spreading and floriferous growth habit, its rapid production of new bulbs, its abundant production of regularly spaced flowers having relatively long peduncles, its natural period of flowering with full production occurring about mid-December, and the attractive coloration of its flowers.

No references cited.

ROBERT E. BAGWILL, Primary Examiner